United States Patent
Klapproth et al.

(10) Patent No.: US 7,250,253 B1
(45) Date of Patent: Jul. 31, 2007

(54) IMMOBILIZATION OF MOLECULES ON SURFACES VIA POLYMER BRUSHES

(75) Inventors: Holger Klapproth, Frieburg (DE); Oswald Prucker, Mainz (DE); Jürgen Rühe, Mainz (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 09/889,935

(22) PCT Filed: Jan. 25, 2000

(86) PCT No.: PCT/EP00/00554

§ 371 (c)(1), (2), (4) Date: Dec. 5, 2001

(87) PCT Pub. No.: WO00/43539

PCT Pub. Date: Jul. 27, 2000

(30) Foreign Application Priority Data

Jan. 25, 1999 (EP) .................................. 99101340
Mar. 3, 1999 (EP) .................................. 99104278

(51) Int. Cl.
C12Q 1/68 (2006.01)
C12M 1/36 (2006.01)
C12N 11/16 (2006.01)
C07H 21/04 (2006.01)

(52) U.S. Cl. .......................... 435/6; 435/7.1; 435/174; 435/283.1; 435/287.2; 536/23.1

(58) Field of Classification Search .................. 435/6, 435/7.1, 174, 283.1, 287; 536/24.3, 25.3; 422/68.1

See application file for complete search history.

(56) References Cited

U.S. PATENT DOCUMENTS 5,143,854 A * 9/1992 Pirrung et al. .............. 436/518

(Continued)

FOREIGN PATENT DOCUMENTS

WO 9005303 5/1990

(Continued)

OTHER PUBLICATIONS

Prucker et al "Synthesis of poly styrene monolayers attached to high surface are silica gels through self-assembled monolayer of azo initiators" Macromolecules, Jan. 22, 1998, 31: 592-601.*

(Continued)

Primary Examiner—B J Forman
(74) Attorney, Agent, or Firm—Bell, Boyd & Lloyd LLP

(57) ABSTRACT

The invention relates to polyfunctional polymer monolayers (polymer brushes) comprising a multitude of polymer chains attached to a surface, with each polymer chain comprising a multitude of units carrying at least on functional group which allows the interaction of the polymer chain with a sample molecule.

4 Claims, 1 Drawing Sheet

U.S. PATENT DOCUMENTS

| | | | | |
|---|---|---|---|---|
| 5,405,746 | A | * | 4/1995 | Uhlen .......................... 435/6 |
| 5,624,711 | A | * | 4/1997 | Sundberg et al. ........... 427/261 |
| 5,919,523 | A | * | 7/1999 | Sundberg et al. ........... 427/333 |
| 6,017,738 | A | * | 1/2000 | Morris et al. .............. 435/91.2 |
| 6,130,037 | A | * | 10/2000 | Lennox et al. ................. 435/6 |
| 6,132,765 | A | * | 10/2000 | DiCosmo et al. ............ 424/450 |
| 6,413,587 | B1 | * | 7/2002 | Hawker et al. ............. 427/264 |
| 6,485,703 | B1 | * | 11/2002 | Cote et al. .................... 424/9.1 |
| 6,497,729 | B1 | * | 12/2002 | Moussy et al. .......... 623/23.57 |

FOREIGN PATENT DOCUMENTS

| | | |
|---|---|---|
| WO | 9704129 | 2/1997 |
| WO | 9741425 | 11/1997 |

OTHER PUBLICATIONS

Prucker et al "Mechanism of radical chain polymerizations initiated by azo compounds covalently bound to the surface of spherical particles" Macromolecules, Jan. 22, 1998, 31: 602-613.*

Anal. Chem. vol. 70, pp. 2731-2736, 1998. Sönksen et al. "Combining MALDI Mass Spectrometry and Biomolecular Interaction Analysis Using a Biomolecular Interaction Analysis Instrument."

Anal. Chem. vol. 69, pp. 4948-4956, 1997. Thiel et al. "In Situ Surface Plasmon Resonance Imaging Detection of DNA Hybridization to Oligonucleotide Arrays on Gold Surfaces."

Polymer vol. 37, pp. 1087-1093. Ribbe et al. "Imaging of polymer monlayers attached to silica surfaces by element specific transmission electron microscopy.", 1996.

* cited by examiner immobilized oligonucleotide strands polymer brush with oligonucleotide
strands (actual sensor device)

IMMOBILIZATION OF MOLECULES ON SURFACES VIA POLYMER BRUSHES

Due to the steadily growing importance of microtechniques in a wide variety of scientific applications, the development of systems which allow the interaction of molecules with surfaces remains a critical issue. Such interactions include the possibility of removing specific molecules from a sample, e.g. to facilitate their analysis/detection, but also of presenting molecules on a surface, thus allowing subsequent reactions to take place. These principles for the immobilization of molecules can be applied in sensor or chromatographic systems or for the provision of modified surfaces in general.

In recent years there have been numerous approaches to fabricate sensor chips which are based on self-assembled monolayers (SAM's) of bifunctional molecules which directly or indirectly couple sample molecules to the sensor surface. Typically, these bifunctional molecules carry a silane or thiol/disulfide moiety in order to achieve a bond with the inorganic surface and an additional functional group (e.g. amino or epoxide groups) which interact with sample molecules, often contained in biological samples in the form of an oligonucleotide, a protein or a polysaccharide etc.

While the formation of a direct bond between the bifunctional compound and the sample molecule is possible, the sample molecules do not necessarily interact directly with the couplers forming the monolayer. Alternatively, appropriate immobilized biomolecules themselves can act as probes for the detection of sample molecules. Such probe molecules can equally be immobilized via a reaction with the free functional groups of the monolayer. In particular, if biomolecules are used as probe molecules, their presence may significantly enhance the specificity of the interaction of the sample molecules with the modified surface. For example, in cases where the fast analysis of a sample of DNA fragments or molecules is required, the monolayers of bifunctional molecules can first be brought in contact with synthetic oligonucleotides which will thus be immobilized. Subsequently, the hybridization of specific molecules, such as compatible strands from a sample is detected, e.g. via fluorescence microscopy, if dye-labeled sample molecules are used.

FIG. 1 shows a schematic description (not to scale) of the design of conventional DNA sensors. Monolayers of usually synthetic oligonucleotide single strands as probes are immobilized on a surface and serve as probe molecules for complementary sample oligonucleotides which are bound via hybridization. The hybridization reaction is, for example, detected via fluorescence originating from appropriate dye labels that are attached to the sample molecules.

Although these techniques are well established for this purpose, the application of standard detection methods is problematic, especially in cases where the surface area available for the detection of one specific type of sample molecules is restricted, e.g. if a variety of molecules is to be analyzed in a parallel process, since the monolayers are limited in their graft density. For example, since the number of hybridized double strands per surface unit of a sensor can not easily be increased, suitable detectors have to meet very high requirements with regard to their sensitivity. Thus, the minimum surface area on a sensor necessary for the detection of one type of oligonucleotide can not be easily reduced. Moreover, the maximum density, i.e. one sample or probe molecule per functional group of the couplers can hardly be attained, since due to sterical hindrance on the two-dimensionally extended monolayer, only a fraction of the functional groups will be able to react with sample or probe molecules. Thus, the overall graft density is low and normally not well defined.

Similar problems with regard to the limited number of reaction sites per surface unit can arise in other applications, where it is desirable to immobilize an increased amount of molecules on a surface.

Various attempts have been made to overcome the problems outlined above. As regards the analysis of oligonucleotides, it has been tried to increase the graft density on the surface by using oligomers or polymers which carry an oligonucleotide strand (or a functional group for its attachment) together with a suitable group which allows the bonding of these oligomers or polymers to the surface of the sensor chip. Due to the increased flexibility of the oligomeric or polymeric chains, a larger fraction of the bifunctional oligomer or polymer molecules which are coupled to the surface is able to immobilize oligonucleotide probe molecules.

However, the total oligonucleotide graft density is not significantly increased, because the graft density of the bifunctional oligomeric or polymeric molecules on the surface is limited. This is a consequence of the fact that the self-assembly of the oligomers or polymers is hindered for kinetic reasons, because once the sensor surface is covered with such molecules, further polymers will have to diffuse against a concentration gradient in order to reach the surface.

Accordingly, it is an object of the present invention to provide a surface which is modified with a polymer monolayer comprising functional groups for the interaction with sample or probe molecules, wherein the number of molecules interacting per surface unit is markedly increased compared to conventional (short chain) monolayers of bifunctional molecules. In addition, the density of available interaction sites should be higher than that obtained from the reaction of bifunctional polymers or oligomers with the surface.

In the specific case of the detection of DNA molecules such as oligonucleotides, the object can be expressed as the provision of a surface with a graft density of synthetic oligonucleotide strands which is higher than that created by coupling the respective oligonucleotides to a functionalized monolayer of low molecular weight couplers. Also, the graft density should be higher then that resulting from the reaction of polymers or oligomers modified with a synthetic oligonucleotide single strand with the surface.

Figure 1:
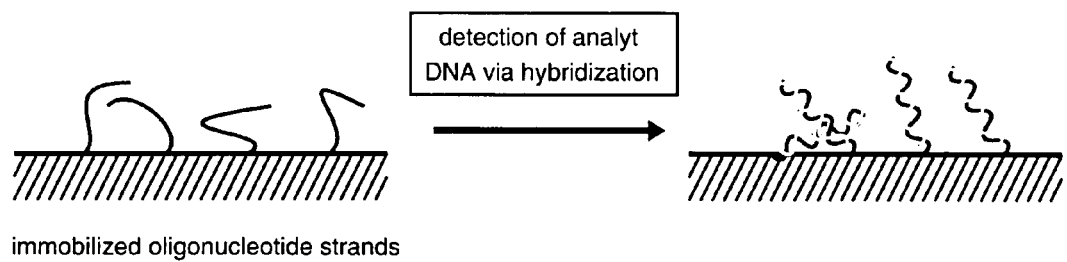
FIG. 1 is a schematic drawing of nucleic acid hybridization.

This object has been achieved by a surface to which an assembly of polymer chains is attached, which comprise each a multitude of functional groups that allow an interaction of the polymer with sample or probe molecules. If, for example, such a polyfunctional polymer chain is used to immobilize one or more synthetic oligonucleotide probes, complementary nucleic acids can subsequently be detected from a mixture of sample molecules after a hybridization reaction has taken place. Surprisingly, it has been found that such an assembly of polyfunctional polymer chains, also referred to as a polymer brush, does not suffer from the problems of conventional detection methods where a high graft density could not be achieved. Moreover, since the flexibility of the polymer chains allows a complete coverage of the sensor surface, surface effects, e.g. during laser scanning, can be avoided.

The term "interaction", as used in this specification includes the formation of covalent bonds, as well as attractive ionic and van-der-Waal's forces and hydrogen bonds. The respective functional moiety within the polymer chain or the probe molecules, which defines the type of interaction, will be selected according to the desired application of the surface according to the invention.

The expression "immobilize" is used hereinafter for an interaction of molecules with the polymer brushes resulting in the formation of a bond which is permanent under the chosen conditions. For example, probe molecules are immobilized by the polymer brushes during their application on a sensor surface. However, by changing conditions (e.g. pH-value, ionic strength) an immobilization may sometimes be reversed.

The term "sample molecule" shall be used herein for molecules which are present in a sample and which couple temporarily or permanently to the polymer chains according to the invention. The present invention includes two general principles for an interaction of the claimed polymer brushes with the sample molecules. In a first embodiment, the functional groups comprised within the polymer chains are chosen in order to allow a direct interaction of the chains with the sample molecules. In a second embodiment, probe molecules are immobilized at the functional groups of the polymer brush, and an interaction takes place between those probe molecules and the sample molecules.

Suitable probe molecules are molecules which are at least bifunctional, so that after their coupling to the multifunctional polymer chains new interaction sites are present in the polymer monolayer according to the invention, which allow an interaction with sample molecules. Preferably, the probe molecules provide highly specific interaction sites for the sample molecules. They can be derived from natural or non-natural sources. Particularly preferred probe molecules are biomolecules such as nucleic acids, including DNA, RNA or PNA (peptide nucleic acid), most preferably oligonucleotides or aptamers, polysaccharides, proteins including glycosidically modified proteins or antibodies, enzymes, cytokines, chemokines, peptidhormones or antibiotics, and peptides. In order to ensure a sufficient stability, e.g. during a sensor application, the probe molecules are preferably covalently bound to the polymer brush.

Depending on use, a multitude of identical probe molecules or a mixture of two or more different probes may be immobilized. For example, a set of identical probe molecules is preferred for the application of the polymer brushes as an affinity matrix.

The polymer monolayer according to the present invention comprises a multitude of single polymer chains which are attached to a surface. Preferably the bond between the polymer chains and the surface is covalent. It is also preferred that the polymer chains are attached to the surface at one of their terminals. The introduction of branched polymers is possible, if desired.

Figure 2:
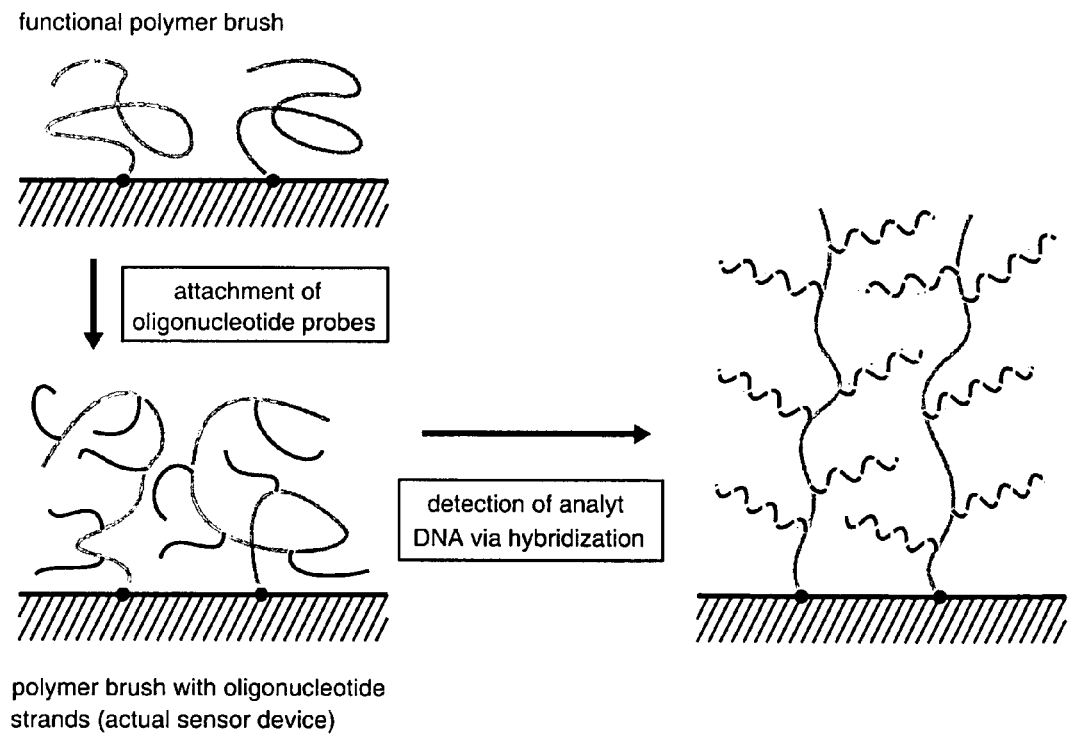
FIG. 2 is a schematic drawing of nucleic acid hybridization using polymer brushes.

FIG. 2 shows a schematic illustration (not to scale) of the design of DNA sensors based on functional polymer brushes. The single stranded oligonucleotides that serve as probe molecules are attached to surface anchored polymer chains. Sample oligonucleotides are detected via hybridization. This reaction can be detected by measuring the significant increase in the layer thickness caused by the incorporation of additional material into the layer.

The polymer chains of the present invention may be homo- or copolymers, depending on the desired application. A homopolymer would be represented by a polymer wherein each of the monomeric units used in polymerization carries at least one of the functional groups which can interact with sample or probe molecules. However, in order to impart certain advantageous properties to the polymer monolayer, a copolymer, formed from these monomers with specific functional groups for the interaction with sample or probe molecules (hereinafter referred to as "functionalized monomers") together with other comonomers can be used.

For example, the reaction of the sample or probe molecules with the polymer is significantly facilitated if the polymer is swellable in the solvent containing these molecules, so that comonomers should preferably be chosen which show a strong interaction with the solvent in question. Since, in a most preferred embodiment of the present invention, biomolecules, which are normally present in aqueous solutions, interact with the polymer chains, said polymer chains are preferably water swellable.

Thus, for example, one or more comonomers can be used which are polar, or even soluble in water, if a homopolymer of functionalized monomers does not show sufficient interaction with water to allow a fast reaction of the molecules to be detected with the functional groups. Both types of monomer, functionalized as well as comonomers, preferably contain a C—C double bond which can react in a radical polymerization reaction. Examples for suitable comonomers which yield a water swellable polymer are acrylic acid, methacrylic acid and derivatives thereof, as e.g. esters and amides of these acids, with alcohols or amines preferably comprising 1 to 12 carbon atoms.

Common examples of this group of monomers are hydroxyethyl methacrylate, acrylamide and dimethyl acrylamide. Another suitable monomer is vinyl pyrrolidon. It is also possible to use monomers that yield at first water insoluble polymers which can then be transferred to water soluble derivatives. A suitable example for this group of polymers is polyvinyl alcohol which can be obtained, for example, by saponification of polyvinyl acetate.

If a copolymer is used, the ratio of comonomers to functionalized monomers is determined prior to the polymerization process in order to define the composition of the resulting polymer chain. Preferably, the ratio of the comonomers to the functionalized monomers ranges from 50/1 to 1/1, more preferably form 20/1 to 2/1.

The functional groups which are necessary to allow a interaction of the polymer layer with the sample or probe molecules are preferably present in side chains of the polymer chains. A "multitude" of functional groups comprised in the polymer chains of the monolayer of the present invention means at least two, but preferably more than two groups per polymer chain. Since the concerned functional groups are preferably comprised in monomers forming the polymer brushes, their number may amount up to several thousand, e.g. up to 10000 of these groups present in a single chain, depending on the size of the probe or sample molecule to be immobilized. Preferably, each chain comprises 20 to 1000 of these functional groups.

Suitable functionalized monomers which are present in the polymer brushes are those monomers which comprise a polymerizable C—C double bond, as well as a further functional moiety that does not take part in the polymerization process. Preferably, this functional group is linked to the main polymer chain via a $C_2$–$C_{10}$, more preferably a $C_3$–$C_7$ alkyl chain as a spacer.

The spacer molecules can be part of the functionalized monomers. Suitable monomers for this approach include acrylic and methacrylic esters or amides of $C_2$–$C_{10}$ alcohols or $C_2$–$C_{10}$ amines. In order to serve as spacers, these alcohols or amines carry an additional functional group at the terminal opposite to the one forming the ester or amide bond. This functional group either represents the one necessary for the interaction with the sample or probe molecules, or can be transformed to such a suitable functional group in a further step.

Alternatively, it is also possible to attach these spacer molecules to suitable reactive segments within the polymer monolayer after its formation. In this case, reactive monomers have to be present during polymerization, such as acrylic or methacrylic acid chlorides or reactive esters thereof, as N-hydroxy succinimides or other monomers, e.g. maleic anhydride. These preferred reactive monomers can form covalent bonds to the bifunctional alcohols or amines that may be used as spacers.

The monomers carrying the spacer unit can readily be synthesized from the respective acrylic or methacrylic acid chloride or anhydride and the ω-amino or hydroxy carboxylic acid. The resulting product can be transformed to the active ester derivative by using e.g. N-hydroxy succinimide. A detailed procedure for the synthesis of several examples of such monomers can be found in the literature e.g., in H.-G. Batz, J. Koldehoff, Macromol. Chem. 177 (1976)683.

As outlined above, it is possible to use reactive monomers which directly yield a polyfunctional polymer monolayer according to the invention. Alternatively, monomers can be chosen which carry a precursor of the functional group to be used on the final surface, e.g. an acid chloride or an acid anhydride. They can subsequently be transformed to reactive groups, e.g. NHS ester or glycidylester groups, which allow an interaction of the polymer with sample or probe molecules under the desired conditions.

Thus, all polymerizable monomers are suitable for the purposes of the present invention, as long as they can be combined with, or comprise, functional groups necessary to allow an interaction of the polymer with the sample molecules or probe molecules.

Functional groups which can be used for the purposes of the present invention are preferably chosen according to the molecules with which an interaction is to be achieved. The interaction can be directed to one single type of sample molecule, or to a variety of sample molecules. Since one important application of the present invention is the detection of specific molecules in biological samples, the functional groups present within the polymer brushes will preferably interact with natural or synthetic biomolecules which are capable of specifically interacting with the molecules in biological samples, leading to their detection. Suitable functional moieties will preferably be able to react with nucleic acids and derivatives thereof; such as DNA, RNA or PNA, e.g. oligonucleotides or aptamers, polysaccharides, proteins including glycosidically modified proteins or antibodies, enzymes, cytokines, chemokines, peptidhormones or antibiotics or peptides or labeled derivatives thereof.

Moreover, it will be possible to conduct the coupling reaction between the molecules to be detected or the synthetic oligonucleotides and the polymer chains under conditions which are not detrimental to the sample or probe molecules. Consequently, in an nucleic acid sensor application, the reaction should be carried out in an aqueous solution, and the temperature should not be raised above 95° C.

Also, the coupling reaction should proceed at a reasonable rate so that the detection can preferably be accomplished within less than 24 hours without requiring extreme pH-values in the solution. For the immobilization of synthetic oligonucleotide single strands, the pH should range between 7 and 11, preferably 7 to 10. During the hybridization reaction of the nucleic acid sample molecules with the probe molecules, the bond between the functional group and the synthetic oligonucleotide single strand as well as the bond of the polymer chain to the substrate has to be able to withstand temperatures of more than 65° C., and a pH of 6–9. In cases where DNA is used as a sample molecule, the temperatures may have to be raised up to about 95° C. in order to effect a separation of the DNA strands, which is necessary for hybridization.

Since most of the probe molecules, especially in biological or medical applications, comprise sterically unhindered nucleophilic moieties, preferred interactions with the polymer brushes comprise nucleophilic substitution or addition reactions leading to a covalent bond between the polymer chains and the sample or probe molecules. For example, synthetical oligonucleotides are usually provided with a free amine group at one end (5' or 3'). Thus, exemplary functional groups provide, for example, a reactive double bond, an equivalent for a double bond (as e.g. an epoxy group) or a reactive leaving group. However, ionic or van-der-Waals forces as well as hydrogen bonds can also be used to couple sample molecules to the polymer brushes if their functional groups are chosen accordingly.

With appropriate functional groups present in the polymer brushes, the polymer monolayers of the present invention can also be used in separation methods, e.g. as a stationary phase in chromatographic applications.

Preferred functional groups can be chosen from prior art literature with respect to the classes of molecules which are to be immobilized and according to the other requirements (reaction time, temperature, pH value) as described above. A general list can for example be found in the text book "Bioconjugate Techniques" by G. T. Hermanson, Academic Press, 1996. In the case of the attachment of amino-terminated oligonucleotides, examples for suitable groups are so-called active or reactive esters as N-hydroxy succinimides (NHS-esters), epoxides, preferably glycidyl derivatives, isothiocyanates, isocyanates, azides, carboxylic acid groups or maleinimides.

As preferred functional monomers which directly result in a polyfunctional polymer monolayer, the following compounds can be employed for the purposes of the present invention:

acrylic or methacrylic acid N-hydroxysuccinimides,
  N-methacryloyl-6-aminopropanoic acid hydroxysuccinimide ester,
  N-methacryloyl-6-aminocapronic acid hydroxysuccinimide ester or
  acrylic or methacryl acid glycidyl esters.

Depending on the application, there is the possibility of providing a polymer brush with a combination of two or more different functional groups, e.g. by carrying out the polymerization leading to the polymer chains in the presence of different types of functionalized monomers. Alternatively, the functional groups may be identical.

The preferred method for the preparation of the polyfunctional polymer monolayer according to the invention is described in the following:

In a first step, the surface is covered by a monolayer of polymerization initiators or starter molecules. The groups in these initiators which allow the initiation of the polymerization are usually chosen e.g. from peroxo groups or azo groups if a thermally initiated radical mechanism is to be used. Aromatic ketones such as benzoin, benzil or benzophenone derivatives are preferably used if the polymers are formed by photochemical initiation. Aromatic ketones comprising sulphur may equally be used, if desired, in order to shift the suitable wavelength for photoinitation to a longer wavelength region. In addition to such labile groups, suitable initiators for the preferred process according to the invention carry one or more groups suitable for their attachment to the surface to be covered by the polymer chains.

The polymer chains according to the present invention are usually grown from the surface via a chain reaction. While radical mechanisms are preferred for practical reasons, the application of ionic polymerization techniques is also possible.

The functional groups comprised in the initiator molecules for surface attachment have to be adapted to the sensor surface used. For the preparation of the initiator monolayer on metal oxides, especially silicon oxide surfaces (evaporated or sputtered $SiO_X$ layers, $SiO_2$ surfaces of silicon wafers, glass, quartz), chlorosilane moieties or alkoxysilanes are used. Thiol or disulfide groups can be employed for the modification of gold surfaces. However, silanes are usually preferred due to their increased stability on surfaces. Moreover, the present invention is not restricted to inorganic surfaces. Organic polymer surfaces can also be used as substrates to carry the polymer monolayers, and there is also the possibility to include the starters for the polymerization reaction directly into such a surface forming polymer.

Preferred examples for initiators which can be used for the purposes of the present invention are listed below, together with their structure formulae:

4,4'-Azobis-(4-cyano pentanoic acid (3'-chlorodimethylsilyl) propyl ester), compound 1 or the respective di- and trichloro or mono-, di- and trialkoxy silane analogs;

2,4'-Azo-(4-cyano pentanoic acid (3"-chlorodimethylsilyl) propyl ester), compound 2 or the respective di- and trichloro or mono-, di- and trialkoxy silane analogs; or the respective compounds with an undecyl spacer rather than an propyl spacer; or disulfide or thiol derivatives of this general type of azo compounds;

4-(3'-chlorodimethylsilyl)propyloxy) benzophenone, 3 or the respective di- and trichloro- or mono-, di- and trialkoxy silane analogs;

silane and disulfide/thiol derivatives of arylazomalodinitriles, such as compound 4.

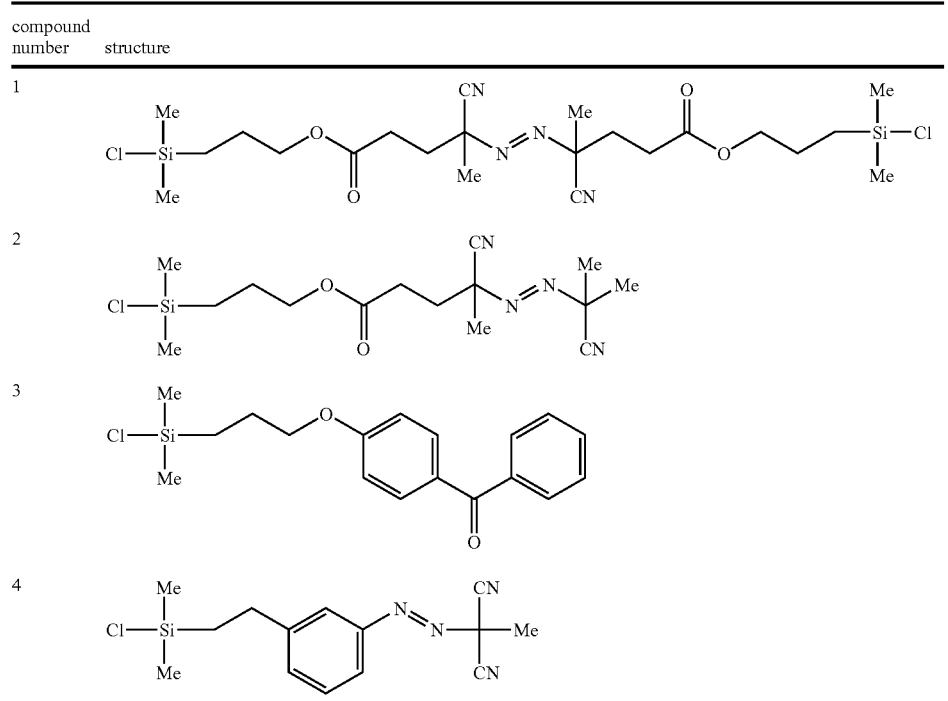

Upon initiation of the polymerization reaction, preferably by a heating step (thermal initiation) or exposure to radiation (photoinitiation) in the presence of polymerizable monomers, polymer chains can be grown from the surface. The polymerization can be carried out under standard reaction conditions known in the art. If this technique is applied, the graft densities of the resulting polymer monolayer can be controlled over a wide range, for example by variation of the polymerization time. Moreover, graft densities can be achieved that are inaccessible by other methods. Thus, polymers can be attached such that the average distance between to anchoring sites on the surface is 5 nm or less, e.g. 2 to 5 nm. Advantageously, such graft densities can be achieved independent of the molecular weight of the attached chains, e.g. even for molecular weights of 100000 g/mol or more.

Furthermore, the preferred in-situ formation of polymer chains on a surface according to the present invention allows the control of the average molecular weight of the attached polymer chains, particularly their length, independent of the graft density. If, e.g., the polymerization is carried out in a solvent where the monomer concentrations can be controlled, a higher monomer concentration will directly lead to a higher molecular weight of the resulting polymers.

According to this precise control of the parameters graft density and molecular weight, it is possible to adapt the properties of the respective polymer layers to a variety of applications. For example, layers of different thickness can be produced over a wide range from a few nanometers up to a few micrometers. It is also possible to fine-tune the properties of the resulting layer, e.g. with respect to the accessibility of the functional groups for subsequently coupled probe and sample molecules which may vary considerably in their size and structure.

The polymer chains obtained via the above preferred method retain a fragment of the initiator in their structure which immobilizes them on the surface, namely the portion starting with the anchoring site and leading to the predetermined point of initiation as it is known in the art for all types of initiators, in particular those mentioned in this application.

Detailed information on the synthesis of initiator molecules, their reaction with surfaces and the preferred conditions of polymerization are described in:

O. Prucker, J. Rühe, Macromolecules, 1998, 31, 592;

O. Prucker, J. Rühe, Macromolecules, 1998, 31, 602 and

O. Prucker, J. Rühe, Langmuir, 1998, 24 (14), 6893.

Care should be taken to remove unreacted monomers as well as non-bonded polymer chains with suitable solvents after polymerization.

Polymer layers prepared according to this method can be applied to a wide variety of surfaces, independent of their shape. Even surfaces which are inaccessible for conventional surface modification methods (e.g. inner surfaces) can be provided with the polymer monolayers according to the invention, since no bulky polymer molecules have to diffuse towards the surface.

Also, it is possible to create patterned arrays of the polymer monolayers by various means. One way are standard photolithographic processes that can either be applied after polymerization (photoablation of the polymers through masks) prior to this step (photodecomposition or photoablation of the initiator monolayer masks) or during the polymerization by means of photopolymerization through masks. Other possible techniques for the creation of patterned polymer monolayers are microcontact printing or related methods, which may be applied during formation of the initiator layer or during polymerization. Finally, ink jet techniques or other microplotting methods can be used to create patterned initiator monolayers which can subsequently be transferred to patterned polymer monolayers. Using any of these techniques, surface structures with dimensions in the micrometer range can be created. The high parallel mode of signal generation and a significant improvement in the integration of analytical data is the most promising feature of such techniques, which accordingly allow the optimization of automatic analytical procedures.

For the detection of a successful immobilization of sample or probe molecules on a polymer monolayer, a variety of techniques can be applied. In particular, it has been found that the polymer layers of the present invention undergo a significant increase in their thickness which can be detected with suitable methods, e.g. ellipsometry. Mass sensitive methods may also be applied.

If nucleic acids, for example oligonucleotides with a desired nucleotide sequence or DNA molecules in a biological sample, are to be analyzed, synthetic oligonucleotide single strands can be reacted with the polymer monolayer. The reaction is carried out under high humidity, preferably in a buffered aqueous solution. The reaction temperature can be raised above room temperature, as long as it is not detrimental to the oligonucleotides. Preferred temperatures are in the range of 40–60° C. In this application, a multitude of identical synthetic oligonucleotide strands or a mixture of different strands can be used. If different strands are used, their sequences should preferably be known.

Before the thus prepared surface is used in a hybridization reaction, unreacted functional groups are deactivated via addition of suitable nucleophiles, preferably $C_1$–$C_4$ amines, such as simple primary alkylamines (e.g. propyl or butyl amine), secondary amines (diethylamine) or amino acids (glycin).

Upon exposure to a mixture of oligonucleotide single strands, e.g. as obtained from PCR, which are labeled, only those surface areas which provide synthetic strands as probes complementary to the PCR product will show a detectable signal upon scanning due to hybridization. In order to facilitate the parallel detection of different oligonucleotide sequences, printing techniques can be used which allow the separation of the sensor surface into areas where different types of synthetic oligonucleotide probes are presented to the test solution.

The term "hybridization" as used in accordance with the present invention may relate to stringent or non-stringent conditions. If not further specified, the conditions are preferably non-stringent. Said hybridization conditions may be established according to conventional protocols described, for example, in Sambrook, "Molecular Cloning, A Laboratory Manual", Cold Spring Harbor Laboratory, N.Y. (1989), Ausubel, "Current Protocols in Molecular Biology", Green Publishing Associates and Wiley Interscience, N.Y. (1989), or Higgins and Hames (Eds) "Nucleic acid hybridization, a practical approach" IRL Press Oxford, Washington D.C., (1985). The setting of conditions is well within the skill of the artisan and to be determined according to protocols described in the art. Thus, the detection of only specifically hybridizing sequences will usually require stringent hybridization and washing conditions such as for example 0.1× SSC, 0.1% SDS at 65° C. Exemplary non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions.

The nucleic acids to be analyzed may originate from a DNA library or a genomic library, including synthetic and semisynthetic nucleic acid libraries. Preferably, the nucleic acid library comprises oligonucleotides.

In order to facilitate their detection in an immobilized state, the nucleic acid molecules should preferably be labeled. Suitable labels include radioactive, fluorescent, phosphorescent, bioluminescent or chemoluminescent labels, an enzyme, an antibody or a functional fragment or functional derivative thereof, biotin, avidin or streptavidin.

Antibodies may include, but are not limited to, polyclonal, monoclonal, chimeric or single chain antibodies or functional fragments or derivatives of such antibodies.

The general methodology for producing antibodies is well-known and has been described in, for example, Köhler and Milstein, Nature 256 (1975), 494 and reviewed in J. G. R. Hurrel, ed., "Monoclonal Hybridoma Antibodies: Techniques and Applications", CRC Press Inc., Boco Raron, Fla. (1982), as well as that taught by L. T. Mimms et al., Virology 176 (1990), 604-619. As stated above, in accordance with the present invention the term "antibody" relates to monoclonal or polyclonal antibodies. Functional antibody fragments or derivatives provide the same specificity as the original antibody and comprise F(ab')$_2$, Fab, Fv or scFv fragments; see, for example, Harlow and Lane, "Antibodies, A Laboratory Manual", CSH Press 1988, Cold Spring Harbor, N.Y. Preferably the antibody of the invention is a monoclonal antibody. Furthermore, in accordance with the present invention, the derivatives can be produced by peptidomimetics. Such production methods are well known in the art and can be applied by the person skilled in the art without further ado.

Depending on the labeling method applied, the detection can be effected by methods known in the art, e.g. via laser scanning or use of CCD cameras.

Also comprised by the present invention are methods where detection is indirectly effected. An example of such an indirect detection is the use of a secondary labeled antibody directed to a first compound such as an antibody which binds to the biological molecule (sample molecule) of interest.

A further application of the polymer monolayers according to the invention lies in the field of affinity chromatography, e.g. for the purification of substances. For this purpose, polymer brushes with identical functional groups or probe molecules are preferably used, which are contacted with a sample. After the desired substance has been immobilized by the polymer brush, unbound material can be removed, e.g. in a washing step. With suitable eluents, the purified substance can then be separated from the affinity matrix.

Preferred substances which may be immobilized on such a matrix are nucleic acid molecules, peptides or polypeptides (or complexes thereof, such as antibodies, functional fragments or derivatives thereof), saccharides or polysaccharides.

A regeneration of the surfaces after the immobilization has taken place is possible, but single uses are preferred in order to ensure the quality of results.

With the present invention, different types of samples can be analyzed with an increased precision and/or reduced need of space in serial as well as parallel detection methods. The sensor surfaces according to the invention can therefore serve in diagnostical instruments or other medical applications, e.g. for the detection of components in physiological fluids, such as blood, serum, sputum etc.

Surfaces according to the present invention can also immobilize starter molecules for synthetic applications in particular in solid phase synthesis, e.g. during the in situ formation of oligo- or polymers. Preferably, the oligo- or polymers are biomolecules and comprise peptides, proteins, oligo- or polysaccharides or oligo- or polynucleic acids. As immobilized initiators, a monomer of these macromolecules can be used.

Moreover, the polymer layers of the present invention can be used as gels in the separation of molecules, preferably biomolecules in an electrical field.

Generally, the present invention allows the provision of homogenically modified surfaces with superior graft density. By choosing the appropriate polymerization conditions, the graft density and the chain length, and thus the thickness of the polymer layer can be controlled. Moreover, structured surfaces can be provided, e.g. by starting the polymerization from patterned arrays of initiator molecules. As a consequence, the polymer monolayers can be adjusted optimally to the respective applications.

The disclosure content of the documents cited throughout the specification are herewith incorporated by reference.

The embodiments of the present invention are further illustrated in the following items:

A preferred process for the detection of sample nucleic acid molecules, preferably of single stranded nucleic acid molecules, using a polymer layer according to the invention comprises the steps of:

a) providing a surface covered with a polyfunctional polymer monolayer according to the invention b) immobilizing suitable probe molecules, preferably oligonucleotide single strands on the polymer monolayer via a reaction with the functional groups present in the polymer chains c) allowing a hybridization reaction to take place between the oligonucleotide single strands and the sample nucleic acid molecules, d) removal of the non-hybridized nucleic acid molecules in a washing step and e) detection of the hybridized nucleic acid molecules, preferably fluorometric.

A preferred process for purifying a compound from a sample, using a polymer layer according to the invention comprises the steps of:

a) providing a surface modified with a polymer monolayer according to the invention b) immobilizing a multitude of identical probe molecules on the polymer layer c) contacting the sample with the resulting polymer layer, under conditions that allow binding of said compound to the probe molecule;

d) and removing material from the sample that has not bound to the probe molecule.

This process may further include the step of e) separating the compound from the probe molecule by use of a suitable eluent.

The following examples illustrate the invention:

(1) Synthesis of the Initiator

As an example, the preparation of compound 1 is described. The reaction pathway is illustrated below. The indices i-iii in the Figure refer to the description of the various steps in the text.

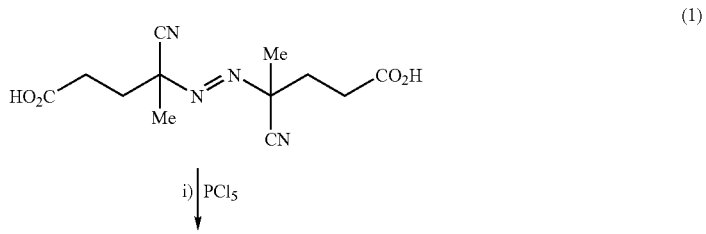

-continued

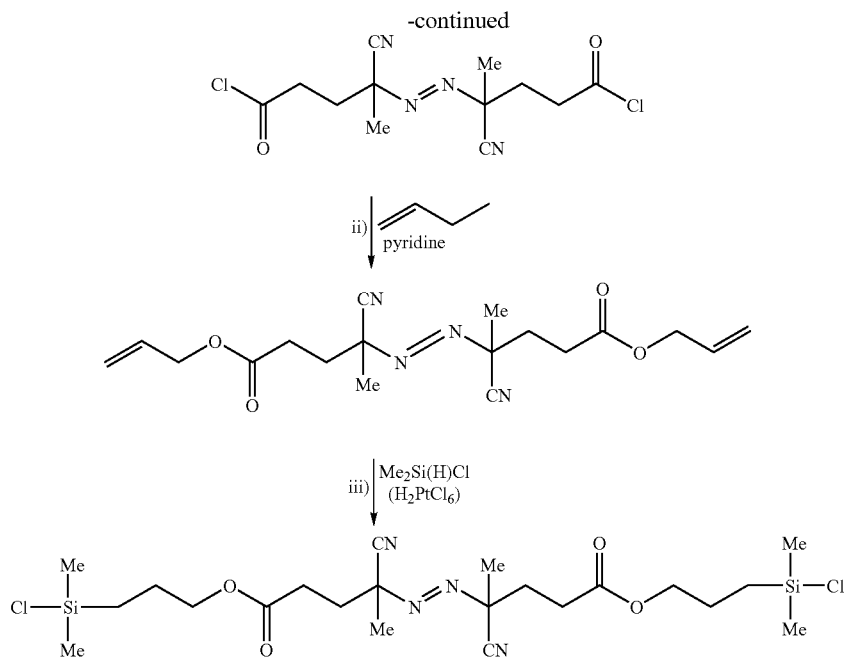

i) To a suspension of 40 g phosphorus pentachloride (PCl$_5$) in 50 ml methylene chloride cooled with an ice-bath was added dropwise a suspension of 10 g of 4,4'-azobis-(4-cyano pentanoic acid) in 50 ml methylene chloride. The mixture was allowed to warm to room temperature and stirred overnight. The excess PCl$_5$ was filtered off and the remaining solution was concentrated until no more PCl$_5$ separated. The mixture was filtered again and the filtrate was added to 300 ml of cold hexane, causing the separation of the acid chloride as a white solid (yield: 90%).

ii) To a solution of 2.7 ml of allyl alcohol and 6.5 ml of pyridine in 50 ml methylene chloride at 0° C. was added dropwise a solution of 10 g of the acid chloride in 50 ml methylene chloride. The mixture was allowed to warm to room temperature and stirred overnight. Then the solution was washed twice with 2N H$_2$SO$_4$, aqueous NaHCO$_3$ and water. The organic layer was dried over Na$_2$SO$_4$ and the solvent was evaporated. The resulting bis allylic ester was recrystallized from methanol (yield: 90%).

iii) To a suspension of 3 g of the bis allylic ester in 30 ml dimethyl chloro silane was added a solution of 30 mg of hexachloroplatinic acid in 0.5 ml of dimethyl ether/ethanol (1/1 v/v), and the mixture was heated to reflux for 3 h. The excess of the silane was evaporated yielding compound 1 as a pale green oil in quantitative yields. Residual platinum catalyst was removed by filtration of a methylene chloride solution of the product over anhydrous Na$_2$SO$_4$.

(2) Formation of an Initiator Monolayer

The initiator synthesized under (1) is immobilized at room temperature on a glass surface under inert conditions (atmosphere of dry nitrogen) using anhydrous toluene as a solvent and dry triethylamine as catalyst. The toluene solution shows a concentration of the initiator of about 50 mmol/l, triethylamine is added up to a concentration of about 10 mmol/l. The samples are kept in the solution overnight and then cleaned by extensive rinsing with methanol and chloroform.

(3) Synthesis of the Functionalized Monomer

As an example, the synthesis of N-methacryloyl-6-aminocapronic acid hydroxysuccinimide ester is described. The reaction pathway is shown below. The indices i-iii in this Figure refer to the description of the various steps in the text.

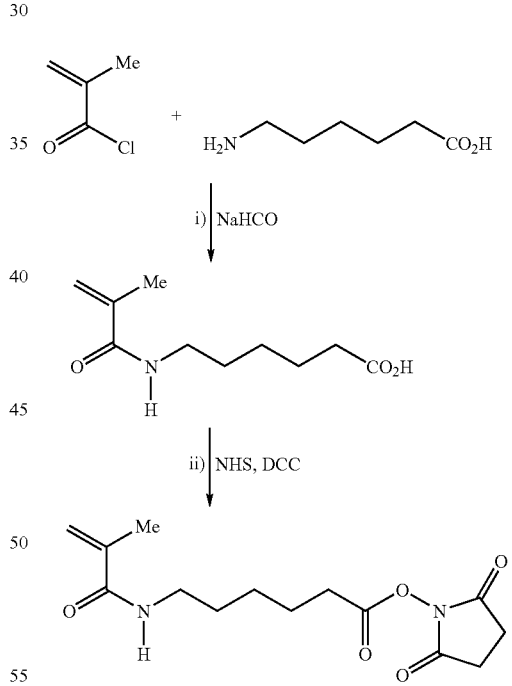

i) A solution of 13.2 g 6-aminocaproic acid and 20 g NaHCO$_3$ in 100 ml water and 50 ml 1,4-dioxane was slowly added to a solution of 10.3 ml of methacrylic acid chloride in 50 ml 1,4-dioxane. The solution was stirred overnight. Then 50 ml of water were added and the mixture was washed three times with 100 ml portions of ethyl acetate. The water layer was acidified (pH 2) with dilute hydrochloric acid and then extracted with three 100 ml portions of ethyl acetate. The combined organic layers were dried over Na$_2$SO$_4$, concentrated to a volume of about 50 ml and added to 350 ml of cold hexane. This mixture was cooled to −20° C., and the product slowly separated overnight as white crystals (yield: ca. 14 g).

ii) A solution of 14 g of the acid in 300 ml methylene chloride was cooled to 5° C. and 8.2 g of N-hydroxy succinimide (NHS) and 14.6 g of N,N-dicyclohexyl carbodiimide were added. The mixture was kept at 5° C. overnight. The precipitate (dicyclohexylurea) was filtered off and the solvent was evaporated. During this step, additional urea separated in some cases and was also filtered off. The crude product was recrystallized from isopropanol to yield about 15 g of the NHS ester monomer.

(4) Formation of a Polyfunctional Polymer Monolayer

A comonomer mixture of N,N-dimethyl-acrylamide (DMAA) and N-methacryloyl-6-aminocapronic acid hydroxy succinimide ester ($C_6AE$) obtained from (3) is polymerized in dimethylformamide (DMF) as solvent. The monomer concentration is 4 mol/l at a molar ratio of the comonomers of $DMAA/C_6AE=5/1$. The polymerization is performed at 60° C. Prior to polymerization, the solutions are carefully degassed through at least 3 freeze-thaw-cycles in order to remove all oxygen traces. After polymerization, every sample is extracted with DMF for at least 10 hours.

(5) Detection of Oligonucleotides Strands

The obtained surface is exposed to 1 nl of a 10 μM oligonucleotide-solution and the coupling reaction is allowed to proceed at about 40–50° C. for two hours in an aqueous solution.

The synthetic oligonucleotide is 5-amino modified, and the solution is buffered with a 100 mM sodium phosphate buffer at a pH of 8.0. After the coupling reaction, the sensor surface is rinsed with the sodium phosphate buffer. In order to define the spatial extension of the specific types of oligonucleotide on the sensor surface for parallel detection, the reactant was printed onto the polymer layer.

The surface thus prepared was allowed to react with a Cy5 labeled PCR product in a buffer of 2×SSC, 10% dextrane sulphate and 50% formamide for 12h at 28° C. The DNA content was 100 ng DNA/80 μl sample. After the hybridization reaction has taken place, the surface was washed in SSC-buffer and the result was detected fluorometrically via laser activation with a CCD camera. A fluorescence signal could only be detected for those areas which carried synthetic oligonucleotides complementary with the PCR product.

What is claimed is:

1. A process for the production of a surface comprising single copolymer chains attached to said surface, wherein each copolymer chain comprises a functional group which allows interaction of the copolymer chain with a sample or probe molecule, comprising the steps of:

a) immobilizing a monolayer of radical polymerization initiator molecules on said surface to produce an initiated surface, wherein each of said initiator molecules comprises a functional group for linkage to the surface and a functional group for subsequent initiation of a polymerization reaction on said initiated surface;

b) initiating polymerization reactions on said initiated surface with (a) a first set of identical or non-identical monomers, each of which comprises (1) at least one functional group which interacts with a sample or probe molecule and (2) at least one C—C double bond, and (b) a comonomer containing at least one C—C double bond, and then c) growing copolymer chains from said initiated surface in the presence of said set of monomers and said comonomer by a radical polymerization chain reaction involving reaction of the C—C double bond of said set of monomers and said comonomer;

wherein the growing of the copolymer chains in step c) linked to said surface results in single copolymer chains attached at a terminus thereof to said surface, and which interact with a sample or probe molecule on said surface.

2. The process according to claim 1, wherein the initiator molecule comprises a chlorosilane, an alkoxysilane, a disulphide or a thiol group.

3. The process according to claims 1 or 2 wherein the initiator molecule comprises a group chosen from azo groups, peroxo groups, or a ketone group in conjugation with an aromatic system.

4. The process according to claim 3, wherein the initiator molecule comprises a group chosen from aromatic ketones or aromatic ketones containing sulphur.

* * * * *